United States Patent
Novak et al.

Patent Number: 5,565,432
Date of Patent: Oct. 15, 1996

[54] SMOOTH MUSCLE CELL PROLIFERATION INHIBITORS

[75] Inventors: Sarah T.A. Novak, Cary, N.C.; Richard M. Soll, Lawrenceville, N.J.

[73] Assignee: American Home Products Corporation, Madison, N.J.

[21] Appl. No.: 335,010

[22] Filed: Nov. 7, 1994

[51] Int. Cl.$^6$ .......... A61K 31/70; A61K 31/705; C07H 15/00
[52] U.S. Cl. .............. 514/25; 514/53; 514/54; 514/56; 536/4.1; 536/123.1; 564/342; 564/343
[58] Field of Search ............ 514/25, 56, 53, 514/54; 536/123.1, 4.1; 564/342, 343

[56] References Cited

U.S. PATENT DOCUMENTS

| | | | |
|---|---|---|---|
| 4,431,636 | 2/1984 | Schaub et al. | 514/25 |
| 4,431,637 | 2/1984 | Upeslacis et al. | 514/25 |
| 4,431,638 | 2/1984 | Schaub et al. | 514/25 |
| 4,435,387 | 3/1984 | Schaub et al. | 514/24 |
| 4,440,758 | 4/1984 | Upeslacis et al. | 514/25 |
| 4,562,485 | 12/1985 | Maeshima | 358/296 X |
| 4,788,599 | 11/1988 | Sugishima | 358/296 |
| 4,870,500 | 9/1989 | Nagashima | 358/443 |
| 5,016,116 | 5/1991 | Maeshima | 358/448 |
| 5,019,562 | 5/1991 | Folkman et al. | 514/58 |
| 5,029,017 | 7/1991 | Abe et al. | 358/451 |
| 5,189,529 | 2/1993 | Ishiwata et al. | 358/451 |

FOREIGN PATENT DOCUMENTS

| | | |
|---|---|---|
| 0312086 | 4/1989 | European Pat. Off. |
| 0312087 | 4/1989 | European Pat. Off. |
| 9309790 | 5/1993 | WIPO |

OTHER PUBLICATIONS

Clowes, et al., J. Vasc. Surg. 13, 885–891 (1991).
Raines et al., Br. Heart J. 69 (Suppl.), S30 (1993).
Isik et al., Am. J. Pathol., 141 (5) 1139–1149 (1992).
Herrman et al., Drugs 46 (1), 18–52 (1993).
Herrman et al., Drugs 46 (1) 249–262 (1993).
Weissberg et al., Cardiovascular Res. 27 1191–1198 (1993).
Castellot et al., Seminars in Thrombosis and Hemostasis, 13 (4), 489–503 (1987).
Borman, Chemical and Engineering News, p. 27, Jun. 28, 1993.
Reilly et al., Drug Development Research, 29, 137–147 (1993).
Casscells, Circulation, 86, 723–729 (1992).
Reidy et al., Endothelial Cell Dysfunction, 31–48, Ed. Plenum Press, NY (1992).
Wight, Arteriosclerosis 1989, 9, 1–20 (1989).
Schmid et al., Seminar in Thrombosis and Hemostasis, 19, Suppl. 1, 155–159 (1993).
Amann et al., Seminars in Thrombosis and Hemostasis, 19, Suppl. 1, 160–163 (1993).
Radhakrishnamurthy et al., Atherosclerosis, 60, 141–149 (1986).

(List continued on next page.)

Primary Examiner—John Kight
Assistant Examiner—Howard C. Lee
Attorney, Agent, or Firm—Steven R. Eck

[57] ABSTRACT

This invention comprises polyanionic benzylglycosides of benzene triacid amides of the general formula I

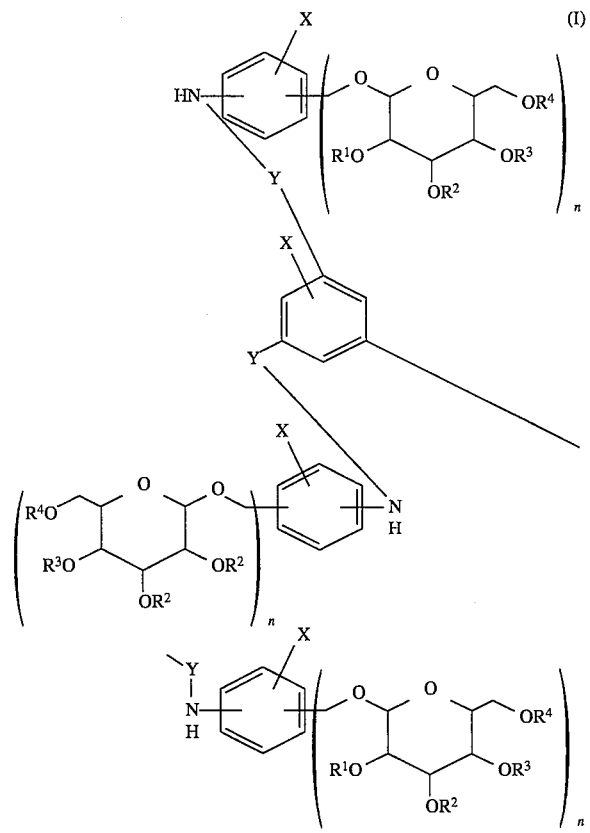

wherein
each of $R^1$, $R^2$, $R^3$, and $R^4$ are, independently, H, $SO_3M$, or

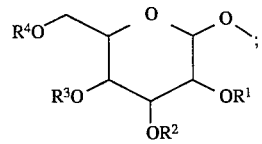

and each oligosaccharide group contains 1 to 3 sugar groups;

M is lithium, sodium, potassium, or ammonium;

n is 1 or 2;

X is a halogen, lower alkyl having 1 to 6 carbon atoms, or lower alkoxy having 1 to 6 carbon atoms;

Y is carbonyl or sulfonyl;

or the pharmaceutically acceptable salts thereof, as well as their use as smooth muscle cell antiproliferation inhibitors and as therapeutic compositions for treating diseases and conditions which are characterized by excessive smooth muscle proliferation.

11 Claims, No Drawings

OTHER PUBLICATIONS

Maffrand et al., Seminars in Thrombosis and Hemostasis, 17, Suppl. 2, 186–198 (1991).

Weisz et al., Angiogenesis: Key Principle–Science–Technology–Medicine p. 107 (1992).

Hermann et al., Arteriosclerosis and Thrombosis, 13, 924–931 (1993).

SMOOTH MUSCLE CELL PROLIFERATION INHIBITORS

This invention relates to novel polyanionic benzylglycosides of benzene triacid amides. More particularly, this invention relates to polyanionic benzylglycosides of benzene triacid amides and their use as smooth muscle cell antiproliferation inhibitors and as therapeutic compositions for treating diseases and conditions which are characterized by excessive smooth muscle proliferation, such as restenosis.

BACKGROUND OF THE INVENTION

Smooth muscle cell (SMC) proliferation is a critical event in the pathogenesis of atherosclerosis and transplant arteriosclerosis as well as in the response to injury arising from all forms of vascular reconstruction such as angioplasty (Raines E. W.; Ross R. *Br. Heart J.* 1993, 69 (Supplement), S 30; Clowes, A. W.; Reidy, M. A. *J. Vasc. Surg* 1991, 13,885; Isik, F. F.; McDonald, T. O.; Ferguson, M.; Yamanaka, E.; Gordon *Am. J. Pathol.* 1992, 141, 1139). However, clinically effective inhibitors of smooth muscle cell proliferation for use as antirestenotic agents have not been successful to date (Herrman, J. P. R.; Hermans, W. R. M.; Vos, J.; Serruys P. W. *Drugs* 1993, 4, 18 and 249).

Reendothelialization of the injured area concurrent with smooth muscle cell proliferation is a major consideration for inhibiting restenosis (Casscells, W. *Circulation* 1992, 86, 722; Reidy, M. A.; Lidner, V. in *Endothelial Cell Dysfunctions*, Simionescu, N. and Simionescu M., Ed. Plenum Press, NY N.Y., (1992), 31). Thus, any successful approach to inhibiting SMC proliferation should not interfere with endothelial cell repair or the normal function of other cell types (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13,489; Wight, T. N. *Arteriosclerosis* 1989, 9, 1). However, the full clinical benefits of heparin, heparin fragments, chemically modified heparin, low molecular weight heparins, and other heparin mimicking anionic polysacchafides may be compromised due to other pharmacological liabilites (excessive bleeding arising from anticoagulation effects, in particular) coupled with heterogenity of the various preparations (Borman, S. *Chemcial and Engineering News*, 1993, June 28, 27; Schmid, K. M.; Preisack, M.; Voelker, W.; Sujatta M.; Karsch, K. R. *Seminars in Thrombosis and Hemostasis* 1993, 19 (Suppl. 1), 155; Amann, F. W.; Neuenschwander, C.; Meyer, B. *Seminars in Thrombosis and Hemostasis* 1993, 19 (Suppl. 1), 160; Radhakrishnamurthy, B.; Sharma, C.; Bhandaru, R. R.; Berenson, G. S.; Stanzani, L.; Mastacchi, R. *Atherosclerosis,* 1986 60, 141; Maffrand, J. P.; Hervert, M. M.; Bernat, A.; Defreyn, G.; Delevassee, D.; Savi, P.; Pinot, J. J.; Sampol, J. *Seminars in Thrombosis and Hemostasis,* 1991, 17 (Suppl. 2), 186). Since the anticoagulant effects of many of these agents are independent of SMC antiproliferative activity, it would be expected that polyanionic agents which are more homogenous in composition and of more defined molecular structure would exhibit a more desirable and balanced profile with fewer side effects associated with aforementioned anionic polysaccharides.

PRIOR ART

WO 92/18546 discloses specific sequences of heparin, obtainable in pure form through synthesis or heparin fragment isolation, which exhibit SMC antiproliferation activity. Beta-Cyclodextrin tetradecasulfate has been described as a smooth muscle cell proliferation inhibitor and as an effective inhibitor of restenosis (Weisz, P. B.; Hermann, H. C.; Joullie, M. M.; Kumor, K.; Levine, E. M.; Macarak, E. J.; Weiner, D. B. *Angiogenesis: Key Principle—Science—Technology—Medicine*—Steiner R., Weisz, P. B.; Langer, R. Eds. Birkhauser Verlag, Basel Switzerland, 1992, pg. 107; Hermann, H. C.; Okada, S. S.; Hozakowska, E.; LeVeen, R. F.; Golden, M. A.; Tomaszewski J. E.; Weisz, P. B.; Barnathan E. S. *Arteriosclerosis and Thrombosis* 1993, 13, 924; Reilly, C. F.; Fujita, T.; McFall, R. C.; Stabilito, I. I.; Wai-si E.; Johnson, R. G. *Drug Development Research* 1993, 29, 137. U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. EP 312087 A2 and EP 312086 A2 discloses antithrombotic and anticoagulant properties of sulfated bisaldonic acid amides.

U.S. Pat. Nos. 4,431,636, 4,431,637, 4,431,638, and 4,435,387 describe polysulphated, thio- and oxy-aryl glycoside derivatives as modulators of the complement system.

The SMC antiproliferative compounds of the present invention differ from all of the prior art in that the SMC antiproliferative compounds (a) are polyanionic benzylglycosides of benzene triacid amides which bear no structural resemblance to heparin, or sulfated cyclodextrins, (b) contain no more than three contiguous sugar residues (trisaccharides) and (b) are of defined structure.

DESCRIPTION OF THE INVENTION

This invention describes the composition and utility of polyanionic benzylglycosides of benzene triacid amides of formula I

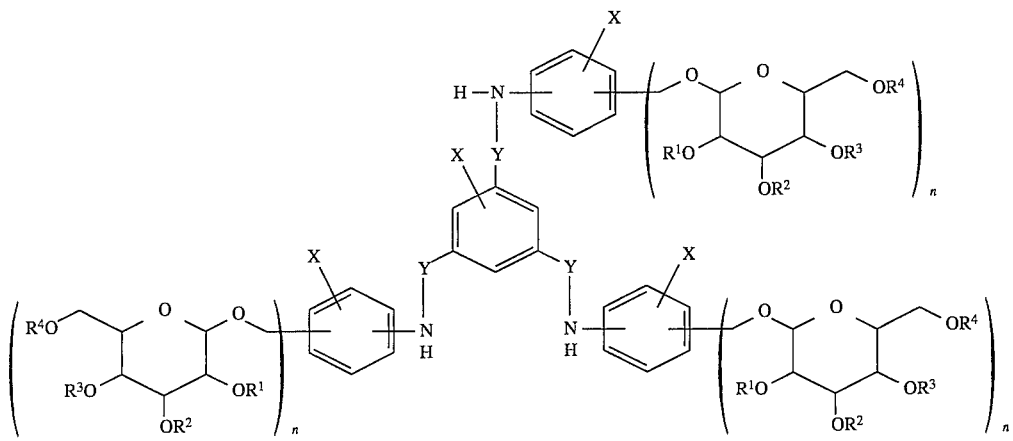

wherein
each of $R^1$, $R^2$, $R^3$, and $R^4$ are, independently, H, $SO_3M$, or

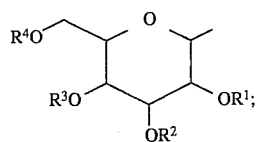

and each monosaccharide or oligosaccharide group contains 1 to 3 sugar or glycoside groups;

M is lithium, sodium, potassium, or ammonium;

n is 1 or 2;

X is a halogen, lower alkyl having 1 to 6 carbon atoms, or lower alkoxy having 1 to 6 carbon atoms;

Y is carbonyl or sulfonyl; or a pharmaceutically acceptable salt thereof.

A more preferred aspect of this invention is the compounds of formula I:

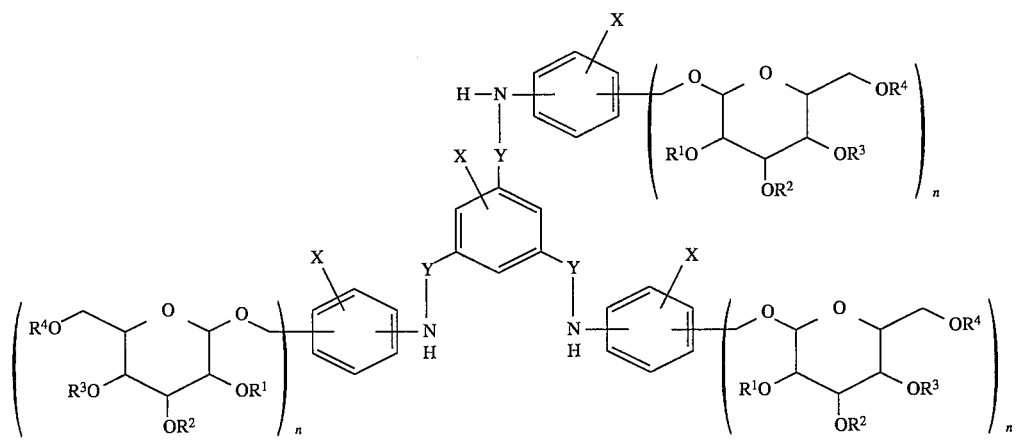

wherein
each of $R^1$, $R^2$, $R^3$, and $R^4$ are, independently, H, $SO_3M$, or

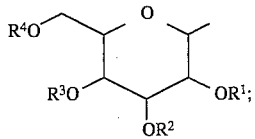

and each oligosaccharide group contains 1 or 2 sugar groups;

M is lithium, sodium, potassium, or ammonium;

n is 1 or 2; X is a halogen, lower alkyl having 1 to 6 carbon atoms, or lower alkoxy having 1 to 6 carbon atoms;

Y is carbonyl;

or a pharmaceutically acceptable salt thereof.

The most preferred compounds of this invention are:

Benzene- 1,3,5-tricarboxylic acid tris{[2-methyl-5-(tetra-O-sulfato-β-glucopyranosyloxymethyl)phenyl]amide} dodecasodium salt or a pharmaceutically acceptable salt thereof;

Benzene- 1,3,5-tricarboxylic acid tris{[2-methyl-5-(hepta-O-sulfato-β-cellobiosyloxymethyl)phenyl]amide} heneicosasodium salt or a pharmaceutically acceptable salt thereof;

Benzene- 1,3,5-tricarboxylic acid tris{[2-chloro-5-(hepta-O-sulfato-β-D-maltosyloxymethyl)phenyl]amide} heneicosasodium salt or a pharmaceutically acceptable salt thereof;

Benzene-1,3,5-tricarboxylic acid tris{[2-chloro-5-(hepta-O-sulfato-β-D-cellobiosyloxymethyl)phenyl]amide} heneicosasodium salt or a pharmaceutically acceptable salt thereof;

Benzene-1,3,5-tricarboxylic acid tris{[2-chloro-5-(hepta-O-sulfato-β-D-lactosyloxymethyl)phenyl]amide} heneicosasodium salt or a pharmaceutically acceptable salt thereof;

Benzene-1,3,5-tricarboxylic acid tris{[3,5-bis-(tetra-O-sulfato-β-D-glucosyloxymethyl)phenyl]amide} tetracosasodium salt or a pharmaceutically acceptable salt thereof;

Benzene-1,3,5-tricarboxylic acid iris {[3,5-bis-(hepta-O-sulfato-β-D-cellobiosyloxymethyl)phenyl]amide} tet-
ratetracontasodium salt or a pharmaceutically acceptable salt thereof.

Process of the Invention

The compounds of the present invention are prepared according to the general sequence of reactions outlined in the Scheme below:

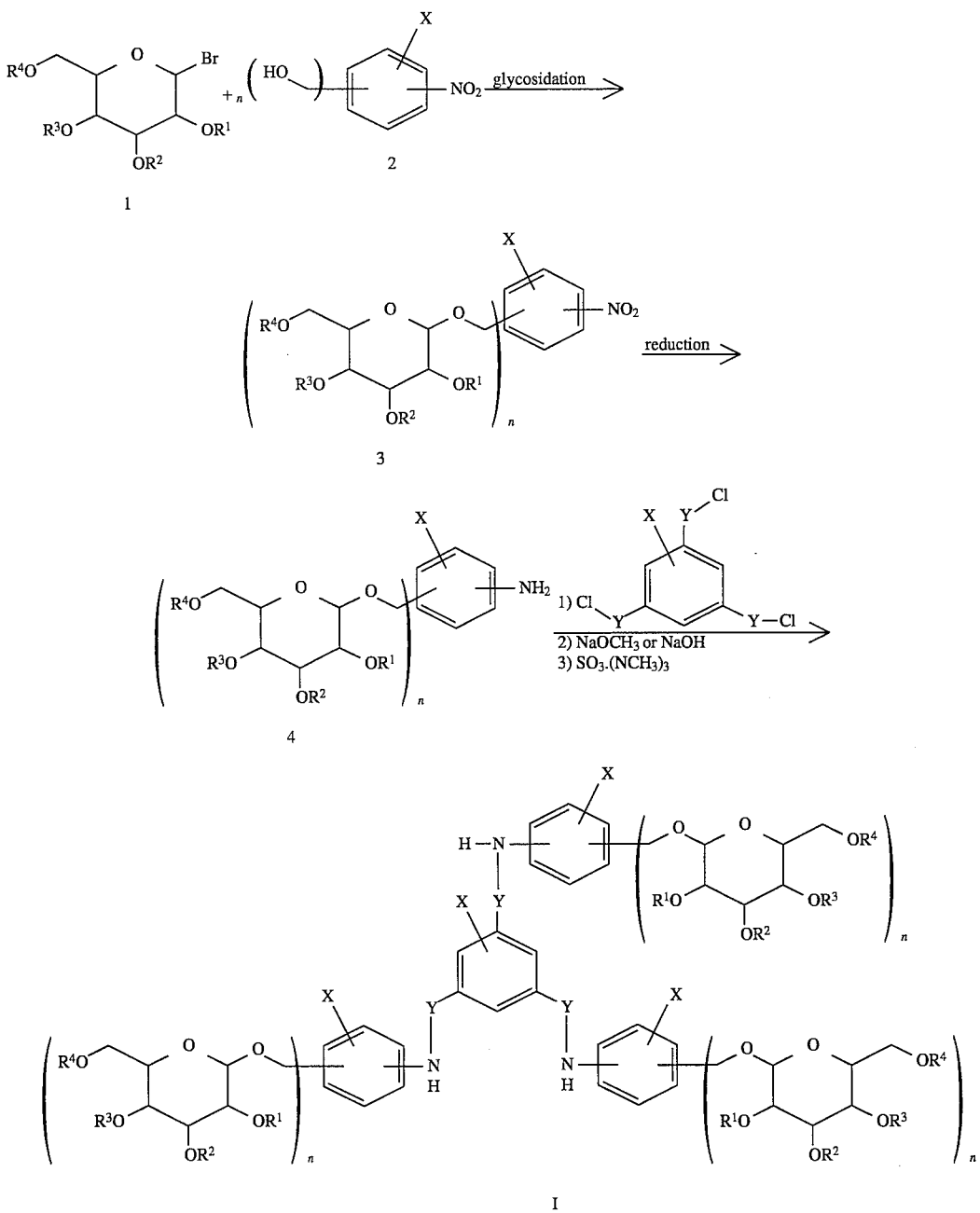

wherein R, n, and X are as defined above.

Thus, a glycosyl bromide 1 is coupled with a benzylic alcohol 2 in the presence of a catalyst such as a mercuric bromide, mercuric cyanide, silver triflate, or silver perchlorate in an aprotic solvent such as dichloromethane, ether, toluene, or nitromethane at temperatures ranging from −40° C. to ambient temperature to yield glycoside 3.

Reduction of the nitro group of 3 with a reducing agent such as stannous chloride is accomplished in a polar aprotic solvent such as ethyl acetate at ambient temperature to reflux, or by catalytic hydrogenation in the presence of a catalyst such as palladium on carbon gives an anilino compound 4.

Coupling of 4 with a benzene triacid chloride or benzene trisulfonyl chloride is completed in the presence of an amine base such as triethylamine or diisopropylethylamine in an aprotic solvent such as dichloromethane or tetrahydrofuran. Hydrolysis of any acetate groups present on the sugars with a base such as sodium methoxide in methanol or aqueous sodium hydroxide in methanol at ambient temperature to reflux, and sulfation of some or all of the free hydroxyl groups on the sugars with a reagent such as sulfur trioxide-trimethylamine complex or sulfur trioxide-pyridine complex in a polar aprotic solvent such as dimethylformamide or dimethylsulfoxide at temperatures ranging from 0° C. to 100° C. yields the target compounds I.

The invention is also directed to pharmaceutical compositions comprised of an effective amount of one or more of the polyanionic benzylglycosides of benzene triacid amides of this invention either alone or in combination with excipients (i.e. pharmaceutically accpetable materials with no pharmacological effect). Such compositions are useful for diseases and conditions which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of the invention are thus useful for treating these diseases and states.

The compounds of this invention may be administered systemically, for example by intravenous injection, typically ranging from 0.1 to 10 mg/ kg/hr over 5–30 days, or by subcutaneous injection at lower dose, by oral administration at higher dose than intravenous injection. Localized delivery of the compounds of this invention may also be achieved by transmembrane, transdermal, or other topical administrative routes using appropriate continuous release devices such as supporting matrix, where applicable. The compositions of the invention may be formulated with conventional excipients, such as a filler, a disintegrating agent, a binder, a lubricant, a flavoring agent and the like. These are formulated in a conventional manner. It is understood that the compounds of this invention may be administered in any manner and at any concentration that is efficacious to the particular recipient. The manner of delivery and composition and concentration of the dose will be determined on an individual basis by the physician or other skilled medical professional treating the recipient.

Effects on Cell Proliferation

A. Cell Sources

The ability of the compounds of the present invention to inhibit smooth muscle cell proliferation and modulate endothelial cell growth was established using isolated aortic cells obtained from commercial sources or, for certain species, prepared in-house. Cell lines used in this study include human and porcine aortic smooth muscle cells and human aortic endothelial cells. Human aortic cell lines were obtained from Clonetics Corporation (San Diego).

Porcine aortas were received from a local slaughterhouse. The material was iced during transit. The aorta was scrupulously cleansed of fatty tissue and rinsed in sterile phosphate-buffered saline with 2% antibiotic/antimycotic (Gibco catalog #600-5240 AG). The tissue was then digested in 10–15 mL of "Enzyme Mixture" containing collagenase type I, 165 U/mL; elastase type III, 15 U/mL; BSA, 2 mg/mL; and soybean trypsin inhibitor, 0.375 mg/mL followed by incubation at 37° C. under 5% $CO_2$ for 10–15 min. After this treatment, the outer surface adventitia was easily removed by peeling with forceps. The aorta was then longitudinally cut and laid open and the endothelial layer was removed by scraping.

The medial layer of cells was rinsed in enzyme solution, and placed in a new 100 mm dish with 10 mL enzyme solution. The aorta was minced using a fine pair of scissors and digested for 2–3 h at 37° C. in 30 mL of fresh enzyme solution. After digestion, the tissue was homogenized using a sterile Pasteur pipette with a fire polished tip or an eppendorf pipetter with a 200–1000 mL sterile pipette tip. The suspension was then centrifuged for 10 min at 8000 rpm and the pellet was suspended in 4–6 mL of fresh medium and plated onto 4–6 100 mm flasks with vented caps. Cells were allowed to grow to confluence and split using 0.25 % trypsin. Cells were evaluated for purity and overall quality using antibody to SMC actin.

B. Effects of Compounds on Cell Proliferation Using $^3$H Thymidine Incorporation Cells were assayed in early passage (generally passage 3–7) at sub-confluent conditions. Cultures were grown in 16 mm (24 well) multi-well culture dishes in media 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, experiments were initiated with the addition of compound, $^3$H thymidine and serum/growth factor to serum deprived synchronized cells and results are reported in this invention accordingly. Growth factor and serum stimulations were optimized for each cell type.

Compounds were added to each well at 50 fold dilution (20 μL/well) and the plates were incubated for 24–36 h at 37° C. in 5% $CO_2$. In this series, all compounds were found to be $H_2O$ soluble and hence, test compounds were initially diluted in $H_2O$ and serially diluted into media. Compounds were routinely assayed at 1, 10, and 100 μM. As a control, grade II porcine intestinal mucosal heparin (sodium salt) from Sigma (H-7005) was routinely assayed in all cell preparations at concentrations from 0.1 to 100 μg/mL.

At the completion of the experiment, plates were placed on ice, washed three times with ice cold PBS and incubated in ice cold 10% trichloroacetic acid (TCA) for 30 min to remove acid soluble proteins. Solution was transferred to scintillation vials containing 0.4N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data was expressed as a percent of control from which $IC_{50}$s could be determined. Compounds of the present invention are effective inhibitors of smooth muscle cell proliferation as summarized in Table I. Furthermore, the compounds of the present invention exhibit human smooth muscle cell (HAOSMC) antiproliferative activity in the case where proliferation is driven by either 10% fetal bovine serum (FBS) or platelet derived growth factor (PDGF; human recombinant PDGF-AB purchased from Upstate Biotechnology Inc., Lake Placid, N.Y.). For example, the sulfated compound of Example 11 inhibits HAOSMC proliferation driven by FBS (IC$_{50}$ 100 nM) as well as by 5 ng/mL of PDGF (IC$_{50}$ 100 nM).

C. Effect on Endothelial Cell Growth vs. Smooth Muscle Cell Proliferation

The promotion of endothelial cell proliferation concurrent with inhibition of smooth cell proliferation is an important consideration for inhibiting the exaggerated response to injury arising from vascular reconstruction. The compounds of the present invention enhance human endothelial cell growth driven by 2% FBS at doses inhibitory towards human smooth muscle cell proliferation driven by 10% FBS as represented by the sulfated compound of Example 11 as shown in FIG. 1.

D. Cytotoxicity

Visually, all cells were found to tolerate high levels of all compounds quite well, however to insure that no toxicity was present, cytotoxicity of compounds was examined using a commercial modification of the MTT assay. Briefly, cells were again grown in 24 well plates to 70–80% confluency and, as before, serum deprived for 24–48 hours prior to initiation of the experimental protocol. To insure that the MTT assay monitored toxicity rather than proliferation, cells were incubated with 250 μM drug in fresh medium without serum for 24 hrs. at 37° C. in a humidified $CO_2$ incubator. Upon completion of the compound treatment, MTT indicator dye was added for 4 hours at 37° C. Cells were then lysed and aliquots from each well were transferred to a 96-well plate for analysis. Absorbance at 570 nm wavelength with a reference wavelength of 630 nm was recorded using an ELISA plate reader. Results are reported as percent viable using no drug (100% viable) and pre-solubilization (0% viable) standards. Sulfated compounds of Examples 8–14 exhibited no toxicity at 250 μM.

E. Anticoagulant Activity

The anticlotting activity of the compounds of this invention were evaluated in a partial thromboplastin time (APTT) assay using normal human plasma collected from 5 donors using the procedure of Fenichel et. al. (*Clin. Chem.* 1964, 10, 69). A BBL Fibrometer automatic precesion coagulation timer utilizing a 0.3 ml probe was employed. An Ellagic acid activated partial thromboplastin was used for these experiments. This reagent is added to human citrated plasma equilibrated at 37° C. in a plastic well in the clot timer. Calcium at 37° C. is added, the clot timer is started and the time for fibrin clot formation (in seconds) was recorded. The effect of the compounds, added to plasma, over a concentration of 12.5–200 μg/mL was determined. Any plasma which did not clot after 240 seconds was assigned a clotting time of 240 seconds. An unfractionated heparin comparator was used over the concentration range of 1.25–10 μg/mL. Clotting tests at all concentrations were run in triplicate. Analysis of variance for a randomized block design was used to determine the significance of differences observed in the clotting times. The potency is reported relative to heparin wherein ratio>1 indicates weaker activity relative to heparin on a μg/mL basis.

TABLE I

| SULFATED COMPOUND OF EXAMPLE | Porcine Smooth Muscle Cell Antiproliferation IC$_{50}$ or (% Inhibition at x concentration) | Anticoagulation Activity (APTT) Relative to Heparin |
| --- | --- | --- |
| 8 | 247 μM | nt |
| 9 | 12.7 μM | no signifcant activity at 25–200 μg/mL |
| 10 | 11.8 μM | nt |

TABLE I-continued

| SULFATED COMPOUND OF EXAMPLE | Porcine Smooth Muscle Cell Antiproliferation IC$_{50}$ or (% Inhibition at x concentration) | Anticoagulation Activity (APTT) Relative to Heparin |
| --- | --- | --- |
| 11 | 2.6 μM | 72 |
| 12 | 2.0 μM | nt |
| 13 | (23–48% at 20 μM) | nt |
| 14 | 3.5 μM | 3.1 | nt = not tested

F. Effect in Experimental Model of Restenosis

Male Sprague-Dawley Rats weighing between 0.3–0.4 kg were housed in polycarbonate cages (2 per box) with corn cob bedding and provided with Purina 5001 rat chow and water (ad. lib. A 12 hr/12 hr light: dark cycle was maintained with light on at 7:00 A.M). After acclimation, rats were randomly assigned to treatment groups (12 per group). The rats were anesthetized with Ketamine, Acepromazone, and Xylazine. The anterior portion of the neck was shaved, a 3 cm incision was made along the midline, and the trachea was exposed by gently parting the underlying tissues and muscle. A retractor was inserted to hold the muscles and tissues aside and the common carotid artery was isolated from the surrounding tissue. A 2 cm segment of the right common carotid artery was lifted such that an 11 mm approximator was placed on the vessel at about 2 and 7 cm before the bifurcation of the internal and external branches of the carotid artery. The 5 mm segment of the common carotid artery between the clamps of the approximator was punctured at about 0.5 mm from the edge of each clamp with a 30 G needle and a gentle stream of isotonic saline was injected through the isolated segment to flush out any blood. A steady stream of air, at a flow rate of 30–35 cc/min, was then directed through the artery for 5 minutes to desiccate the vessel. The approximator was loosened initially to remove air from the segment and then removed to restore blood flow. Gentle pressure was applied to the neck until bleeding stopped. The neck incision was sutured closed and the animal returned to individual housing (polycarbonate boxes with corn cob bedding).

A sham operation was performed on a control group of rabbits in which the carotid artery was exposed but not subjected to air drying.

Experimental drugs were administered i.v. from ALZA 2 ml 2 osmotic pumps for 2 weeks starting 2 days before air drying. A 12 mm incision was made along the posterior midline of the rat's neck. To insert the pumps, a subcutaneous pocket was formed through the incision along the animal's back and the pump was implanted in the pocket and the attached cannula was pulled subcutaneously to the anterior neck where it was inserted into the jugular vein contralateral to the injured arterial vessel.

Two weeks following surgery, the rats were sacrificed via anesthetized exsanquination. The injured arterial tissue was fixed in situ by perfusion with $Zn^{2+}$ Formalin, then removed for histological processing and evaluation. Arterial tissue was cut in 5 micron sections at 200 to 500 micron intervals. The cross sections were photographed and the arterial media and intima were digitized and measured. These values were used to determine the intima/media (I/M) ratio; group differences were compared by ANOVA. The compounds of the present invention have been found to be effective inhibitors of intimal thickening in this experimental model of restenosis. For example the sulfated compound of Example 11 inhibited intimal thickening by 50% in comparison to untreated animals at a dose of 125 µg/mL according to the procedure described above.

Specific procedures are described in the following examples. These examples are given to illustrate the invention and should not be construed as limiting the invention set forth in the appended claims.

EXAMPLE 1

Step 1

5-(Tetra-O-acetyl-β-glucopyranosyloxymethyl)-2-methyl-1-nitrobenzene

A solution of 10.3 g (61.5 mmol) of 4-methyl-3-nitrobenzyl alcohol, 30.3 g (73.7 mmol) of acetobromoglucose, 13.3 g (51.7 mmol) of Hg(CN)$_2$, and 18.6 g (52.0 mmol) of HgBr$_2$ in nitromethane (150 mL) was stirred at room temperature for 20 h. The reaction mixture was quenched with 250 mL of 2.0 M KBr and then extracted into CH$_2$Cl$_2$. The organic phase was washed with sat. NaHCO$_3$ and brine. The organic phase was dried over MgSO$_4$, concentrated to an oil and semi-purified by flash chromatography using petroleum ether/ethyl acetate (2:1). Solvent removal provided a total of 16.4 g (54% yield) of the title compound as a colorless solid: $^1$H-NMR (CDCl$_3$, 300 MHz) δ 7.92 (d, 1 H), 7.43 (dd, 1 H), 7.33 (d, 1 H), 5.06–5.24 (m, 3 H), 4.92 (d, 1 H), 4.66 (d, 1 H), 4.59 (d, 1 H), 4.28 (dd, 1 H), 4.18 (dd, 1 H), 3.68–3.72 (m, 1 H), 2.60 (s, 3 H), 2.11 (s, 3 H), 2.07 (s, 3 H), 2.03 (s, 3 H), and 2.01 ppm (s, 3 H).

Step 2

5-(Tetra-O-acetyl-β-glucopyranosyloxymethyl)-2-methylphenylamine

A solution of 5-(tetra-O-acetyl-β-glucopyranosyl-oxymethyl)-2-methylnitrobenzene (6.73 g, 13.5 mmol) in EtOAc (150 mL) containing 21.4 g (94.8 mmol) of SnCl$_2$ dihydrate was stirred at 75° C. for 3 h. The reaction mixture was cooled and quenched with ca. 450 mL of sat. NaHCO$_3$, diluted with CH$_2$Cl$_2$, and filtered through solka floc. The organic phase of the tiltrate was dried (MgSO$_4$), and concentrated to give yellow solid which was washed with a little Et$_2$O to provide 3.85 (63% yield) of the title compound: $^1$H-NMR (CDCl$_3$, 300 MHz) δ 7.02 (d, 1 H), 6.64 (s, 1 H), 6.63 (d, 1 H), 5.02–5.17 (m, 3 H), 4.79 (d, 1 H), 4.50–4.55 (m, 2 H), 4.29 (dd, 1 H), 4.17 (dd, 1 H), 3.64–3.68 (m, 1 H), 2.18 (s, 3 H), 2.11 (s, 3 H), 2.02 (s, 3 H), 201(S, 3 H), and 2.00 ppm (s, 3 H).

EXAMPLE 2

Step 1

5-(Hepta-O-acetyl-β-D-cellobiosyloxymethyl)-2-methyl-1-nitrobenzene

The title compound was prepared in 47% yield by the procedure of step 1 of Example 1 using 4-methyl-3-nitrobenzyl alcohol and acetobromocellobiose as well as sat. NaCl in the quenching step. Purification was achieved by flash chromatography (EtOAc/petroleum ether, 1:2 to 1:1 to 2:1): $^1$H-NMR (CDCl$_3$, 300 MHz) δ 7.91 (s, 1 H), 7.40 (d, 1 H), 7.32 (d, 1 H), 4.80–5.20 (m, 6 H), 4.40–4.80 (m, 4 H), 4.36 (dd, 1 H), 4.02–4.13 (m, 2 H), 3.81 (t, 1 H), 3.60–3.68 (m, 2 H), 2.60 (s, 3 H), 2.14 (s, 3 H), 2.08 (s, 3 H), 2.06 (s, 3 H), 2.03 (s, 3 H), 2.02 (s, 3 H), 2.01 (s, 3 H) and 1.98 ppm (s, 3 H).

Step 2

5-(Hepta-O-acetyl-β-D-cellobiosyloxymethyl)-2-methylphenylamine

The title compound, mp 180–182 ° C., was prepared in 62% yield from 5-(hepta-O-acetyl-β-D-cellobiosyloxymethyl)-2-methyl-1-nitrobenzene using the procedure of step 2 of Example 1. Purification was achieved by flash chromatography (EtOAc/petroleum ether, 1:1 to 2:1): $^1$H-NMR (DMSO-d$_6$, 400 MHz) δ 5 6.86 (d, $^1$ H), 6.48 (d, 1 H), 6.36 (dd, $^1$ H), 5.24 (t, 1 H), 5.10 (m, 1H), 4.80–4.90 (m, 3 H), 4.61–4.72 (m , 2 H), 4.56 (d, 1 H), 4.30–4.31 (m, 2 H), 4.22 (dd, 1 H), 4.08 (dd, 1 H), 3.99–4.03 (m, 1 H), 3.94 (dd, 1 H), 3.73–3.81 (m, 2 H) 2.10 (s, 3 H), 2.10 (s, 3 H), 2.00 (s, 3 H), 1.98 (s, 3 H), 1.96 (s, 3 H), 1.95 (s, 3 H), 1.94 (s, 3 H), and 1.91 ppm (s, 1 H); mass spectrum (+FAB) m/z 778. Anal. Calcd. for C$_{34}$H$_{46}$NO$_{18}$: C, 53.97; H, 6.13; N, 1.85. Found: C, 53.67; H, 5.92; N, 1.62.

EXAMPLE 3

Step 1

5-(Hepta-O-acetyl-β-D-cellobiosyloxymethyl)-2-chloro-1-nitrobenzene

The title compound was prepared in 45% yield by the procedure described in step 1 of Example 1 using 4-chloro-3-nitrobenzyl alcohol and acetobromocellobiose as well as sat. NaCl in the quenching step: $^1$H-NMR (CDCl$_3$, 300 MHz) δ 7.82 (d 1H), 7.53 (d, 1 H), 7.42 (dd, 1 H), 4.8–5.2 (m, 5 H), 4.73 (d, 1 H), 4.51–4.66 (m, 4 H), 4.3–4. 4. (m, 1 H), 4.03–4.11 (m, 2 H), 3.81 (t, 1 H), 3.60–3.68 (m, 2 H) 2.13 (s, 3 H), 2.09 (s, 3 H), 2.06 (s, 3 H), 2.03 (s, 3 H), 2.01 (s, 3 H), 2.01 (s, 3 H), 1.99 (S, 3 H) and. 1.57 ppm (s, 3 H).

Step 2

5-(Hepta-O-acetyl-β-D-cellobiosyloxymethyl)-2-chloro-phenylamine

The title compound was prepared from 5-(hepta-O-acetyl-β-D-cellobiosyloxymethyl)-2-chloro-1-nitrobenzene in 61% yield as a solid by trituration with ether using the procedure of step 2 of Example 1: $^1$H-NMR (CDCl$_3$, 300 MHz) δ 7.20 (d, 1 H), 6.75 (s, 1 H), 6.60 (d, 1 H), 4.89–5.19 (m, 5 H), 4.73 (d, 1 H) 4.47–4.60 (m, 4 H), 4.36 (dd, 1 H), 4.02–4.13 (m, 2 H), 3.80 (t, 1 H), 3.55–3.67 (m, 2 H), 2.14 (s, 3 H), 2.08 (s, 3 H), 2.03 (s, 3 H), 2.02 (s, 6 H), 2.01 (s, 3 H), and 2.00 ppm (s, 3 H).

EXAMPLE 4

Step 1

5-(Hepta-O-acetyl-β-maltosyloxymethyl)-2-chloro-1-nitrobenzene

The title compound was prepared in 50% yield by the procedure described in step 1 of Example 1 using 4-chloro-3-nitrobenzyl alcohol and acetobromomaltose as well as sat. NaCl in the quenching step. Purification was achieved by flash chromatography (CH$_2$Cl$_2$:EtOAc (5:1) to provide the title compound: partial $^1$H-NMR (CD1$_3$; 300 MHz) δ 7.83 (d, 1 H), 7.53 (d, 1 H), 7.42 (dd, 1 H), 5.42 (d, 1 H), 5.36 (t, 1 H), 5.06 (t, 1 H), 2.15 (s, 3 H), 2.11 (s, 3 H), 2.04 (s, 3 H), 2.03 (s, 3 H), 2.02 (s, 3 H), and 2.01 ppm (s, 3 H).

13

Step 2

5-(Hepta-O-acetyl-β-maltosyloxymethyl)-2-chloro-phenylamine

The title compound was prepared from 5-(hepta-O-acetyl-β-maltosyloxymethyl)-2-chloro-1-nitrobenzene in 96% yield by the procedure of step 2 of Example 1. The crude product was obtained as a solid and was used without further purification: partial $^1$H-NMR (CDl$_3$; 300 MHz) δ 7.20 (d, 1 H), 6.73 (d, 1 H), 6.60 (dd, 1 H), 5.41 (d, 1 H), 5,30–5.39 (m, 2 H), 5.23 (t, 1 H), 5.05 (t, 1 H), 4.83–4.89 (m, 2 H), 4.74 (d, 1 H), 2.16 (s, 3 H), 2.11 (s, 3 H), 2.032 (s, 3 H), 2.027 (s, 3 H), and 2.00 ppm (s, 6 H).

EXAMPLE 5

Step 1

5-(Hepta-O-acetyl-β-lactosyloxymethyl)-2-chloro-1-nitrobenzene

The title compound was prepared in 51% yield by the procedure described in step 1 of Example 1 using 4-chloro-3-nitrobenzyl alcohol and acetobromolactose as well as sat. NaCl in the quenching step. Purification was achieved by an intial flash chromatography (CH$_2$Cl$_2$:EtOAc (4:1) and then re-flash rechromatography (CH$_2$Cl$_2$:EtOAc (9:1)) to provide the title compound as a solid: partial $^1$H-NMR (CDl$_3$; 300 MHz) δ 7.82 (d, 1 H), 7.53 (d, 1 H), 7.42 (dd, 1 H), 5.35 (d, 1 H), 5.21 (s, 1 H), 4.87 (d, 1 H), 4.66 (d, 1 H), 2.15 (s, 3 H), 2.13 (s, 3 H), 2.06 (s, 6 H), 2.05 (s,6H), and 1.97 ppm (s, 3 H).

Step 2

5-(Hepta-O-acetyl-β-lactosyloxymethyl)-2-chloro-phenylamine

The title compound was prepared from 5-(hepta-O-acetyl-β-lactosyl-oxymethyl)-2-chloro-1-nitrobenzene in 94% yield by the procedure 1 of step 2 of Example 1. The crude product was obtained as a solid and was used without further purification: partial $^1$H-NMR (CDl$_3$; 300 MHz) δ 7.19 (d, 1 H), 6.72 (d, 1 H), 6.59 (dd, 1 H), 5.35 (d, 1 H), 5.08–5.20 (m, 2 H), 4.73 (d, 1 H), 2.15 (s, 3 H), 2.14 (s, 3 H), 2.06 (s, 3 H), 2.05 (s, 3 H), 2.02 (s, 3 H), and 1.97 ppm (s, 3 H).

EXAMPLE 6

Step 1

3.5-Bis,(hepta-O-acetyl-β-D-cellobiosyloxymethyl), 1-nitrobenzene

The title compound was prepared in 42% yield by the procedure described in step 1 of Example 1 using 1 equivalent of 5-nitro-m-xylene-α,α'-diol, two equivalents of acetobromocellobiose, and two equivalents of all other reagents as well as sat. NaCl in the quenching step. Purification was achieved initially by flash chromatography (EtOAc/CH$_2$Cl$_2$ (3:1)) and then by trituration from ether: $^1$H-NMR (CDCl$_3$, 300 MHz) δ 8.10 (s, 2 H), 7.48 (s, 1 H), 4.88–5.30 (m, 12 H), 4.68 (d, 2 H), 4.52–4.59 (m, 6 H), 4.38 (dd, 2 H), 4.0–4.13 (m, 4 H), 3.82 (t, 2 H), 3.58–3.68 (m, 4 H), 2.13 (s, 6 H), 2.08 (s, 6 H), 2.07 (s, 6 H), 2.03 (s, 12 H), 2.01 (s, 6 H), and 1.98 ppm (s, 6 H).

14

Step 2

3,5-Bis-(hepta-O-acetyl-β-D-cellobisyloxymethyl)phenylamine

The title compound was prepared in 54% yield by procedure of step 2 of Example 1 using 3,5-bis-(β-D-cellobiosyloxymethyl)-1-nitrobenzene. Purification was achieved using EtOAc/petroleum ether (1:1): $^1$H-NMR (CDCl$_3$, 300 MHz) δ 6.73 (bs, 2 H), 6.67 (bs, 1 H), 5.03–5.30 (m, 6 H), 4.97 (d, 2 H), 4.91 (d, 2H), 4.75 (d, 2 H), 4.49–4.61 (6 H), 4.37 (dd, 2 H), 4.02–4.13 (m, 6 H), 3.81 (t, 2 H), 3.57–3.69 (m, 4 H), 2.15 (s, 6 H), 2.08 (s, 6 H), 2.03 (s, 6 H), 2.01 (s, 18 H), and 1.98 ppm (s, 6 H).

EXAMPLE 7

Step 1

3,5-Bis(tetra-O-acetyl-β-D-glucosyloxymethyl)-1-nitrobenzene

The title compound was prepared by the procedure described in step 1 of Example 1 using 1 equivalent of 5-nitro-m-xylene-α,α'-diol, two equivalents of acetobromoglucose, and two equivalents of all other reagents as well as sat. NaCl in the quenching step. Purification was achieved by flash chromatography (EtOAc/CH$_2$Cl$_2$ (1:4 to 1:2) to give a 29% yield of nearly pure title compound which was used without further purification.

Step 2

3.5-Bis(tetra-O-acetyl-β-D-glucosyloxymethyl)phenylamine

The title compound was prepared by the procedure of step 2 of Example 1 using 5.29 g 3, 5-bis-(tetra-O-acetyl-β-D-glucosyloxymethyl)-1-nitrobenzene. Purification was achieved by flash chromatography (CH$_2$Cl$_2$/EtOAc (3:2)) to give 2.00 g (39% yield) of the title compound as a yellow oil: partial $^1$H-NMR (CDCl$_3$. 300 MHz) δ 6.56 (s, 3 H), 5.0–5.2 (m, 6 H), 4.8 (d, 2 H), 4.4–4.6 (m, 4 H), 3.7 ppm (brd, 2 H).

EXAMPLE 8

Step 1

Benzene-1,3,5-tricarboxylic Acid. Tris{[2-methyl-5-(β-glucopyranosylxymethyl)Phenyl]amide}

To a solution of 5-(tetra-O-acetyl-β-glucopyranosyloxymethyl)-2-methylphenylamine (1.51 g, 3.22 mmol) and 3.22 mmol of triethylamine in THF (35 mL) was added 285 mg (1.01 mmol) of benzene-1,3,5-tricarboxylic acid chloride. The reaction mixture was stirred for 4 h, quenched with MeOH, diluted with CH$_2$Cl$_2$, and washed with H$_2$O. The organic phase was dried (MgSO$_4$) and concentrated to an oil which was purified by flash chromatography (CH$_2$Cl$_2$:EtOAc (1:1) to give crude product. (1.17 g, 70% yield). To a solution of 983 mg (0.631 mmol) of the crude material in MeOH (25 mL) was added 1N NaOH (9.47mL, 9.47 mmol). After stirring at 50° C. for 3 h, the reaction mixture was quenched with 1N HCl (7.58 mL, 7.58 mmol) and the product isolated by filtration. Drying in vacuo provided 700 mg (100% yield) of crude title compound. The solid was suspended in H$_2$O to remove additional salts to provide pure title compound, mp>200° C.: $^1$H-NMR (DMSO-d$_6$, 400 MHz) δ 10.3 (s, 3 H), 8.73 (s, 3 H), 7.37 (s, 3 H), 7.28 (d, 3 H), 7.23 (d, 3 H), 5.10 (bs, 3 H), 4.84 (d, 3

H), 4.57 (d, 3 H), 4.25 (d, 3 H), 3.69 (dd, 3 H), 3.44–349 (m, 3 H), 3.0–3.2 (m, 6 H), and 2.28 ppm (s, 9 H); $^{13}$C-NMR (DMSO-$d_6$; 100 MHz) δ 164.6, 136.1, 135.3, 133.0, 130.3, 129.8, 126.0, 125.7, 102.1, 77.0, 76.8, 73.6, 70.2, 69.2, 61.2, and 17.8 ppm; mass spectrum (–FAB) m/e 1052.3, 890.3; IR (KBr) 1650 cm$^{-1}$. Anal. Calcd. for $C_{51}H_{63}N_3O_{21}$.4 $H_2O$: C, 54.40; H, 6.35; N, 3.73. Found: C, 54.44; H, 6.15; N, 3.68.

Step 2

Benzene-1,3,5-Tricarboxylic Acid Tris{[2-methyl-5-(tetra-O-sulfato-β-glucopyranosyloxymethyl) phenyl]amide)}Dodecasodium Salt A solution of benzene-1,3,5-tricarboxylic acid tris-{[2-methyl-5-(β-glucopyranosyloxymethyl) phenyl]-amide}(761 mg, 0.748 mmol) and sulfur trioxide (6.24 g, 44.9 mmol) in DMF (30 mL) was stirred at 70° C. for 4 days. The reaction mixture was quenched at room temperature with $H_2O$ and concentrated. Purification was achieved by Sephadex G-10 chromatography ($H_2O$ elution) followed by cation ion exchange using a column of Dowex 50×8 strongly acidic resin (Na form) to provide 825 mg (48% yield) of the title compound as colorless solid, mp>200° C.: $^1$H-NMR ($D_2O$, 400 MHz) δ 8.73 (s, 3 H), 7.46–7.51 (bm, 9 H), 4.97–5.00 (m, 6 H), 4.87 (d, 3 H), 4.76 (t, 3 H), 4.47–4.53 (m, 6 H), 4.22–4.27 (m, 3 H), 4.15–4.19 (m, 3 H), and 2.37 ppm (s, 9 H); $^{13}$C-NMR ($D_2O$; 100 MHz) δ 168.3, 135.3, 135.2, 135.0, 134.3, 131.1,. 130.0, 128.1, 127.0, 99.1, 76.2, 75.9, 73.4, 72.6, 70.7, 67.8, and 16.8 ppm; mass spectrum (electrospray) (m–zNa)/z 736.5 (m–3 Na)$^{3-}$, 546.2 (m–4 Na)$^{4-}$, and 433.4 (m–5 Na)$^{5-}$. Anal. Calcd. for $C_{51}H_{51}N_3Na_{12}O_{51}S_{12}$.12$H_2O$: C, 24.55; H, 3.01; N, 1.68; S, 15.40 Found: C, 24.29; H, 2.78; N, 2.69; S, 15.84.

EXAMPLE 9

Step 1

Benzene-1,3,5-Tricarboxylic Acid Tris{[2-methyl-5-(β-cellobiosyloxymethyl) Phenyl]Amide}

To a solution of 5-(tetra-O-acetyl-β-cellobiosyloxymethyl)-2-methylphenylamine (1.49 g, 1.97 mmol) and 217 μL/(1.97 mmol) of triethylamine in THF (35 mL) was added 174 mg (0.66 mmol) of benzene-1,3,5-tricarboxylic acid chloride. The reaction mixture was stirred for 4 h, quenched with MeOH, diluted with $CH_2Cl_2$, and washed with $H_2O$. The organic phase was dried ($MgSO_4$) and concentrated to an oil which was purified by trituration with ether to give 873 mg (55% yield) of an off-white solid. To a solution of the crude material in MeOH (25 mL) was added 1N NaOH (9.1 mL, 9.1 mmol). After stirring at 50° C. for 3 h, the reaction mixture was quenched with 1N HCl (7.64 mL, 7.64 mmol) and the product isolated by filtration. Drying in vacuo provided 408 mg (80% yield) of title compund. mp>200° C.: partial $^1$H-NMR (DMSO-$d_6$, 400 MHz) δ 10.33 (s, 3 H), 8.75 (s, 3 H), 7.36 (s, 3 H), 7.27 (d, 3 H), 7.23 (d, 3 H), 5.2–5.3 (br, 6 H), 5.00 (br, 3 H), 4.84 (d, 3 H), 4.70 (s, 3 H), 4.56–4.64 (m, 9 H), 4.33 (d, 3 H), 4.26 (d 3 H), 3.77 (dd, 3 H), 3.64–3.70 (m, 6 H), and 2.27 ppm (s, 9 H): $^{13}$C-NMR (DMSO-$d_6$; 100 MHz) δ 164.5, 136.0, 135.9, 135.1, 133.0, 130.2, 129.8, 125.9, 125.6, 103.2, 101.8, 80.5, 76.8, 76.4, 75.0, 74.9, 73.3, 73.2, 70.0, 69.4, 61.0, 60.4, and 17.8 ppm; mass spectrum ((–)-FAB) 1539.2 (m).

Step 2

Benzene- 1,3,5-tricarboxylic Acid Tris{[2-methyl-5-(hepta-O-sulfato-β-cellobiosyloxymethyl) phenyl]amide}Heneicosasodium Salt A solution of 279 mg( 149 mmol) of benzene-1,3,5-tricarboxylic acid tris-{[2-methyl-5-(β-cellobiosyloxymethyl)phenyl]amide}and sulfur trioxide trimethylamine complex (3.19 g) in DMF (30 mL) was stirred at 70° C. for 4 days. The reaction mixture was quenched at room temperature with $H_2O$ and concentrated in vacuo. The residue was purified by Sephadex G-10 chromatography ($H_2O$ elution). Cation exchange was effected using a column of Dowex 50×8 strongly acidic resin (Na form) to provide 357 mg of the title compound as a tan solid, mp>200° C.: partial $^1$H-NMR ($D_2O$, 400 MHz) δ 8.70 (s, 3 H), 7.44–7.52 (m, 9 H), 4.99 (d, 3 H), 4.97 (d, 3 H), 4.86 (d, 3 H), 4.83 (d, 3 H), 4.68 (d, 3 H), 4.64 (d, 3 H), 4.58 (dd 3 H) 4.01–4.04 (m, 6 H), and 2.34 ppm (s, 9 H); $^{13}$C-NMR ($D_2O$; 100 MHz) δ 168.17, 135.4, 135.0, 134.9, 134.2, 131.0, 129.9, 127.9, 126.7, 99.9, 99.2, 77.6, 77.34, 77.31, 77.02, 74.3, 73.6, 73.4, 73.0, 70.6, 67.6, 66.5, and 16.7 ppm; mass spectrum (electrospray) (m–z Na)/z 897.8 (m–4 Na)$^{4-}$, 713.2 (m–5 Na)$^{5-}$, and 590.8 (m–6 Na)$^{6-}$. Anal Calcd. for $C_{69}H_{72}N_3Na_{21}O_{99}S_{21}$.18$H_2O$: C, 20.67; H, 2.70; N, 1.05; S, 16.78. Found: C, 20.35; H, 2.78 N, 1.00; S, 14.19.

EXAMPLE 10

Step 1

Benzene-1,3,5-tricarboxylic Acid Tris{[5-(hepta-O-acetyl-β-D-maltosyloxymethyl)-2-chlorophenyl]amide}

To a solution of 962 mg (1.24 mmol) of 5-(hepta-O-acetyl-β-maltosyloxymethyl)-2-chlorophenylamine in THF (20 mL) containing 173 μL/(1.24 mmol) of triethylamine was added 110 mg (0.413 mmol) of benzene-1,3,5-tricarboxylic acid chloride. The reaction mixture was stirred for 90 min, quenched with MeOH, diluted with $CH_2Cl_2$, and washed with $H_2O$. The organic phase was dried ($MgSO_4$) and concentrated to a light yellow solid. Purification by flash chromatography ($CH_2Cl_2$:EtOAc (2:1 to 1:1) gave 607 mg (59% yield) of the title compound as a colorless solid, mp 132° C. (dec): partial $^1$H-NMR (CDCl$_3$, 400 MHz) δ 8.66 (s, 3 H), 8.65 (s, 3 H), 8.48 (d, 3 H), 7.42 (d, 3 H), 7.08 (dd, 3 H), 5.40 (d, 3 H), 5.33 (t, 3 H), 5.23 (t, 3 H), 5.03 (t, 3 H), 4.82–4.93 (m, 9 H), 4.66 (d, 3 H), 4.62 (d, 3 H), 4.53 (dd, 3 H), 3.67–3.70 (m, 3 H), 2.14 (s, 3 H), 2.10 (s, 3 H), 2.04 (s, 3 H), 2.01 (s, 3 H), 1.99 (s, 3 H), 1.995 (s, 3 H), 1.986 (s, 3 H), and 1.97 ppm (s, 3 H): 13C-NMR (CDCl$_3$; 100 MHz) δ 170.5; 170.2, 169.9, 169.7, 169.4, 162.9, 137.0, 136.1, 134.1, 129.2, 128.9, 124.2, 123.1,121.1, 99.1, 95.5, 75.4, 72.6, 72.2, 72.0, 70.1, 70.0, 69.3, 68.5, 68.0, 62.8, 61.5, 20.9, 20.7, 20.6, and 20.5 ppm; mass spectrum (positive (Ca$^{2+}$) electrospray) 1262 (m+Ca$^{2+}$)/2. Anal. Calcd. for $C_{108}H_{126}Cl_3N_3O_{57}$.1 $H_2O$: C, 51.83; H, 5.16; N, 1.68. Found: C, 51.64; H, 5.11; N, 1.53.

Step 2

Benzene-1,3,5-tricarboxylic Acid Tris{[2-chloro-5-(β-D-maltosyloxymethyl)-phenyl]amide}

To a solution of 983 mg (0.194 mmol) of benzene-1,3,5-tricarboxylic acid tris{[5-(hepta-O-acetyl-β-D-maltosyloxymethyl)-2-chlorophenyl]amide} in MeOH (15 mL) was added 1N NaOH (4.67 mL, 4.67 mmol). After stirring at 50° C. for 4 h, the reaction mixture was quenched with 1N HCl (4.08 mL, 4.08 mmol) and the product isolated by filtration. Drying in vacuo provided 309 mg (99% yield) of title compund. mp>200° C.: partial $^1$H-NMR (DMSO-$d_6$, 400 MHz) δ 10.56 (s, 3 H), 8.78 (s, 3 H), 7.60 (d, 3 H), 7.56 (d, 3 H), 7.37 (dd, 3 H), 5.02 (d, 3 H), 4.89 (d, 3 H), and 4.63 ppm (d, 3 H); $^{13}$C-NMR (DMSO-$d_6$; 100 MHz) δ 164.57, 137.83, 134.73, 134.61, 130.13, 129.36, 128.67, 127.53, 126.85, 102.12, 100.75, 79.54, 76.37, 75.28, 73.45, 73.24, 73.02, 72.42, 69.87, 68.72, 60.76, and 60.64 ppm; mass spectrum ((−)-FAB) m/z 1598.4 (M−H), 1436.3, and 1274.3. Anal. Calcd. for $C_{66}H_{84}Cl_3N_3O_{36} \cdot 9H_2O$: C, 44.94; H, 5.83; N, 2.38. Found: C, 44.48; H, 5.46; N, 2.78.

Step 3

Benzene-1,3,5-tricarboxylic Acid Tris{[2-chloro-5-(hepta-O-sulfato-β-D-maltosyloxymethyl)phenyl]amide}Heneicosasodium Salt A solution of benzene-1,3,5-tricarboxylic acid tris-{[2-chloro-5-(β-D-maltosyloxymethyl)phenyl]amide} (208 mg, (130 mmol) and sulfur trioxide trimethylamine complex (1.90 g) in DMF (20 mL) was stirred at 70° C. for 2.5 days. The reaction mixture was quenched at room temperature with $H_2O$ and concentrated in vacuo. The residue was purified by Sephadex G-10 chromatography ($H_2O$ elution). Cation exchange was effected using a column of Dowex 50×8 strongly acidic resin (Na form) to provide 400 mg (82% yield) of the title compound as a tan solid, mp>178° C. (dec): partial $^1$H-NMR ($D_2O$, 400 MHz) δ 8.74 (s, 3 H), 7.67–7.70 (m, 6 H), 7.57 (d, 3 H), 5.62 (d, 3 H), 5.09 (d, 3 H), 5.04 (d, 3 H), 4.66 (t, 3 H), 4.61 (dd, 3 H), and 4.52 ppm (t, 3 H); $^{13}$C-NMR ($D_2O$; 100 MHz) δ 168.1, 136.9, 134.7, 132.9, 130.3, 130.1, 129.7, 128.6, 127.6, 98.8, 94.1, 77.4, 76.0, 74.8, 73.4, 73.2, 72.3, 71.8, 69.9, 69.7, 67.6, and 66.1 ppm; mass spectrum (electrospray) (m−z Na)/z 1225.0 (m−3 Na)$^{3-}$, 912.8 (m−4 Na)$^{4-}$, 725.6 (m−5 Na)$^{5-}$, and 601 (m−6 Na)$^{6-}$. Anal. Calcd. for $C_{66}H_{63}Cl_3N_3Na_{21}O_{99}S_{21} \cdot 4 Na_2SO_4 \cdot 21 H_2O$: C, 16.90; H, 2.25; N, 0.90, S, 17.09. Found: C, 16.77; H, 2.29; N, 0.97; S, 16.90.

EXAMPLE 11

Step 1

Benzene-1,3,5-tricarboxylic Acid Tris{[5-(hepta-O-acetyl-β-D-cellobiosyloxymethyl)-2-chlorophenyl]amide}

To a solution of 1.43 g (1.85 mmol) of 5-(hepta-O-acetyl-β-cellobiosyloxymethyl)-2-chlorophenylamine in THF (25 mL) containing 254 μL (1.85 mmol) of triethylamine was added 163 mg (0.615 mmol) of benzene-1,3,5-tricarboxylic acid chloride. The reaction mixture was stirred for 90 min, quenched with MeOH, diluted with $CH_2Cl_2$, and washed with $H_2O$. The organic phase was dried ($MgSO_4$) and concentrated to an off-white solid. Purification by flash chromatography ($CH_2Cl_2$:EtOAc (1:1)) gave 937 mg (62% yield) of product. An analytical sample, obtained as a white crystal (mp>200° C.), was prepared from a separate run: $^{13}$C-NMR ($CDCl_3$; 100 MHz) δ 170.5, 170.4, 170.2, 169.8, 169.6, 169.3, 169.0, 163.0, 137.0, 136.1, 134.0, 129.2, 128.9, 124.7, 123.2, 121.2, 100.75, 99.4, 76.37, 72.90, 72.8, 72.47, 71.93, 71.59, 71.46, 70.1, 67.8, 61.8, 61.5, 20.87, 20.66, 20.60, and 20.50 ppm; mass spectrum (positive ($Ca^{2+}$) electrospray) (m+Ca)$^{2+}$/2 1262. Anal. Calcd. for $C_{108}H_{126}Cl_3N_3O_{57} \cdot 2 H_2O$: C, 51.46; H, 5.20; N, 1.67. Found: C, 51.44; H, 4.88; N, 1.71.

Step 2

Benzene, 1,3,5-tricarboxylic Acid Tris{[2-chloro-5-(β-D-cellobiosyloxymethyl)phenyl]amide}

A solution of 917 mg (0.375 mmol) of benzene-1,3,5-tricarboxylic acid tris{[5-(hepta-O-acetyl-β-D-cellobiosyloxymethyl)-2-chlorophenyl]amide} in MeOH (25 mL) was treated with 9.0 mL (9.0 mmol) of 1N NaOH. After stirring for 3 h at 50° C., the reaction mixture was quenched at room temperature with 1N HCl (7.9 mL, 7.9 mmol) and stirred for 10 min. The solid was collected and dried in vcauo to provide 579 mg (96% yield) of the title compound as colorless solid, mp>200° C.: partial $^1$H-NMR (DMSO-$d_6$, 400 MHz) δ 10.57, (s, 3 H) 8.78 (s, 3 H), 7.58 (s, 3 H), 7.55 (d, 3 H), 7.36 (s, 3 H), 4.87 (d, 3 H), 4.34 (d, 3 H), 4.25 (d, 3 H), 3.77 (d, 3 H), and 3.68 ppm (d, 3 H); $^{13}$C-NMR (DMSO-$d_6$; 100 MHz) δ 164.6, 137.9, 134.7, 134.6, 130.2, 129.4, 128.7, 127.5, 126.9, 103.2, 102.0, 80.5, 76.8, 76.5, 75.0, 73.3, 73.2, 70.0, 68.8, 61.0, and 60.4 ppm; IR (KBr) 1655 cm$^{-1}$; mass spectrum (+FAB) m/z 1622.2 (M+Na). Anal. Calcd. for $C_{66}H_{84}Cl_3N_3O_{36} \cdot 5 H_2O$: C, 46.86; H, 5.60; N, 2.48. Found: C, 46.84; H, 5.46; N, 2.37.

Step 3

Benzene-1,3,5-tricarboxylic Acid Tris[2-chloro-5-(hepta-O-sulfo-β-D-cellobiosyloxymethyl)phenyl]amide) Heneisosasodium Salt A soluiton of 403 mg (0.252 mmol) of benzene-1,3,5-tricarboxylic acid tris{[2-chloro-5-(β-D-cellobiosyloxymethyl)phenyl]amide} and sulfur trioxide trimethylamine complex (3.89 g, 28 mmol)in DMF (25 mL) was stirred at 70° C. for 5 days. The reaction mixture was quenched at room temperature with $H_2O$ and concentrated in vacuo. The residue was purified by Sephadex G-10 chromatography ($H_2O$ elution). Cation exchange was effected using a column of Dowex 50×8 strongly acidic resin (Na form) to provide 949 mg of the title compound as a tan solid, mp>178° C. (dec): partial $^1$H-NMR ($D_2O$, 400 MHz) δ 8.73 (s, 3 H), 7.70 (s, 3 H), 7.67 (d, 3 H), 7.57 (d, 3 H), 4.99–5.03 (m, 6 H), 4.68 (t, 3 H), 4.64 (t, 3 H), 4.60 (dd, 3 H), 4.24 (d, 3 H), 4.20 (t, 3 H), and 4.02–4.05 ppm (m, 3 H); $^{13}$C-NMR ($D_2O$; 100 MHz) δ 168.1, 139.0, 134.7, 132.8, 130.3, 130.0, 129.6, 128.5, 127.4, 99.9, 99.4, 77.5, 77.4, 77.3, 77.0, 74.3, 73.7, 73.3, 73.1, 70.1, 67.6, and 66.6 ppm. Anal. Calcd. for $C_{66}H_{63}Cl_3N_3Na_{21}O_{99} \cdot 33 H_2O$: C, 18.28; H, 2.93; N, 0.97; S, 15.53. Found: C, 18.20; H, 2.67; N, 0.76; S, 15.51. Capillary electrophoresis showed purity in excess of 98%.

EXAMPLE 12

Step 1

Benzene-1,3,5-Tricarboxylic Acid Tris{[2-chloro-5-(β-D-lactosyloxymethyl)phenylamide}

To a solution of 993 mg (1.28 mmol) of 5-(hepta-O-acetyl-β-lactosyloxymethyl)-2-chloro-phenylamine in THF (20 mL) containing 178 μL (1.28 mmol) of triethylamine was added 113 mg (0.427 mmol) of benzene-1,3,5-tricarboxylic acid chloride. The reaction mixture was stirred for 90 min, quenched with MeOH, diluted with $CH_2Cl_2$, and washed with $H_2O$. The organic phase was dried ($MgSO_4$) and concentrated to an off-white solid. Purification by flash chromatography ($CH_2Cl_2$:EtOAc (2:1 to 1:1)) gave 431 mg (41% yield) of product. A solution of 431 mg (0.174 mmol) of the compound in MeOH (15 mL) was treated with 4.2 mL (4.2 mmol) of 1N NaOH. After stirring for 4 h at 50° C., the reaction mixture was quenched at room temperature with 1N HCl (3.6 mL, 3.6 mmol). The solid was collected and dried in vacuo to provide 193 mg (69% yield) of the title compound as colorless solid, mp>200° C.: partial $^1$H-NMR (DMSO-$d_6$, 400 MHz) δ 10.58 (s, 3 H), 8.79 (s, 3 H), 7.59 (d, 3 H), 7.56 (d, 3 H), 7.36 (dd, 3 H), 4.88 (d, 3 H), 4.63 (d, 3 H), 4.35 (d, 3 H), 4.20 (d, 3 H), 3.79 (d, 3 H), and 3.11 (s, 3 H) $^{13}$C-NMR (DMSO-$d_6$; 100 MHz) δ 164.6, 137.8, 134.7, 134.6, 130.2, 129.4, 128.7, 127.5, 126.8, 103.8, 102.0, 80.7, 75.5, 75.0, 74.9, 73.22, 73.19, 70.5, 68.8, 68.1, 60.5, and 60.3 ppm; mass spectrum ((−)-FAB) m/z 1598.8 and 1600.8 (both M-H). Anal. Calcd. for $C_{66}H_{84}Cl_3N_3O_{36}$·9 $H_2O$: C, 44.94; H, 5.83; N, 2.38. Found: C, 44.24; H, 5.38; N, 2.29.

Step 2

Benzene-1,3,5-tricarboxylic Acid Tris-{[2-chloro-5-(hepta-O-sulfato-β-D-lactosyloxymethyl)phenyl]amide} Heneicosasodium Salt A soluiton of 126 mg (0.079 mmol) of benzene-1,3,5-tricarboxylic acid tris{[2-chloro-5-(β-D-lactosyloxymethyl)phenyl]amide} and sulfur trioxide trimethylamine complex (1.5 g, 8.26 mmol) in DMF (20 mL) was stirred at 70° C. for 2.5 days. The reaction mixture was quenched at room temperature with $H_2O$ and concentrated in vacuo. The residue was purified by Sephadex G-10 chromatography ($H_2O$ elution). Cation exchange was effected using a column of Dowex 50×8 strongly acidic resin (Na form) to provide 207 mg (70% yield) of the title compound as a tan solid, mp>171° C. (dec): partial $^1$H-NMR ($D_2O$; 400 MHz) δ 8.73 (s, 3 H), 7.68 (s, 3 H), 7.67 (d, 3 H), 7.58 (d, 3 H), 5.13 (d, 3 H), 5.08 (d, 3 H), 5.01 (d, 3 H), 4.43 (t, 3 H), and 4.24 ppm (t, 3 H); $^{13}$C-NMR ($D_2O$; 100 MHz) δ 168.1, 137.0, 134.7, 132.8, 130.3, 130.1, 130.0, 129.6, 128.5, 127.5, 100.9, 99.2, 77.6, 77.0, 75.6, 75.3, 75.04, 74.97, 73.2, 71.7, 70.0, 66.5, and 66.3 ppm; mass spectrum (electrospray (m−zNa)/z 913 (M−4Na)$^{4-}$ and 725.9 (M−5 Na)$^{5-}$ Anal. Calcd. for $C_{66}H_{63}Cl_3N_3Na_{21}O_{99}S_{21}$·21 $H_2O$: C, 19.23; H, 2.57; N, 1.02; S, 16.33. Found: C, 19.51; H, 2.61; N, 1.11; S, 15.97.

EXAMPLE 13

Step 1

Benzene-1.3.5-tricarboxylic Acid Tris{[3,5-bis-(tetra-O-acetyl-b-D-glucopyranosyloxymethyl)phenyl]amide}

To a solution of 861 mg (1.06 mmol) of 3, 5-bis(tetra-O-acetyl-β-D-glucosyloxymethyl)phenylamine in THF (20 mL) containing 147 μL (1.06 mmol) of triethylamine was added 93.6 mg (0.353 mmol) of benzene-1,3,5-tricarboxylic acid chloride. The reaction mixture was stirred for 90 min, quenched with MeOH, diluted with $CH_2Cl_2$, and washed with $H_2O$. The organic phase was dried ($MgSO_4$) and concentrated to a light yellow solid. Purification was achieved by trituration with ether to provide 849 mg (0.327 mmol) of the title compound as colorless crystals, mp 120–129° C.: $^1$H-NMR (CDCl$_3$; 400 MHz) δ 9.1 (bs, 3 H), 8.73 (s, 3 H), 7.67 (s, 6 H), 6.99 (s, 3 H), 5.18 (t, 6 H), 5.10 (t, 6 H), 5.03 (dd, 6 H), 4.84 (d, 6 H), 4.65 (d, 6 H), 4.61 (d, 6 H), 4.27 (br s, 12 H), 3.72–3.74 (m, 6 H), 2.06 (s, 18 H), 2.01 (s, 36 H), and 1.97 ppm (s, 18 H); $^{13}$C-NMR (CDCl$_3$; 100 MHz) δ 6 171.2, 170.2, 169.4, 163.9, 138.4, 138.2, 135.7, 129.2, 123.1, 119.5, 100.1, 72.8, 71.9, 71.3, 71.1, 68.4, 62.0, 20.8, 20.64, and 20.56 ppm. Anal. Calcd. for $C_{117}H_{141}N_3O_{63}$·2$H_2O$: C, 53.36; H, 5.55; N, 1.60. Found: C, 53.29; H, 5.29; N, 1.61.

Step 2

Benzene-1,3,5-tricarboxylic Acid Tris{[3,5-bis-(tetra-O-sulfato-β-D-glucosyloxymethyl)phenyl]amide} tetracosasodium Salt A solution of 780 mg (0.300 mmol) of benzene-1,3,5-tricarboxylic acid tris{[3,5-bis-(tetra-O-acetyl-β-D-glucopyranosyloxymethyl)phenyl]amide} in MeOH (15 mL) containing 8.1 mL (8.1 mmol) of 1N NaOH was stirred at 50° C. for 5 h. The reaction mixture was cooled to room temperature and quenched with 1N HCl (7.2 mL, 7.2 mmol). The product, benzene-1,3,5-tricarboxylic acid tris{[3,5-bis-(β-D-glucosyloxymethyl)phenyl]amide}, was collected (338 mg, 81% yield) and used directly in the next reaction: partial $^1$H-NMR (DMSO-$d_6$; 400 MHz) δ 10.73 (s, 3 H), 8.74 (s, 3 H), 7.78 (s, 6 H), 7.22 (s, 3 H), 4.88 (d, 6 H), 4.57 (d, 6 H), 4.29 (d, 6 H), 3.71 (d, 6 H), and 3.48 (dd, 6 H); $^{13}$C-NMR (DMSO-$d_6$; 100 MHz) δ 164.5, 138.7, 138.4, 135.3, 129.8, 123.0, 119.1, 102.2, 77.0, 76.8, 73.5, 70.1, 70.0, and 61.1 ppm.

A solution of 317 mg (0.200 mmol) of benzene-1,3,5-tricarboxylic acid tris{[3,5-bis-(β-D-glucosyloxymethyl)phenyl]amide} and sulfur trioxide trimethylamine complex (3.59 g, 25.8 mmol) in DMF (25 mL) was stirred at 70° C. for 3 days. The reaction mixture was quenched at room temperature with $H_2O$ and concentrated in vacuo. The residue was purified by Sephadex G-10 chromatography ($H_2O$ elution) to give a yellow solid, which by NMR contained some residual trimethylammonium sulfate. Cation exchange was effected using a column of Dowex 50×8 strongly acidic resin (Na form) to provide 771 mg (ca. 95% yield) of the title compound, mp 174° C., as coloress solid: $^1$H-NMR ($D_2O$; 400 MHz) δ 8.63 (s, 3 H), 7.68 (br s, 6 H), 7.44 (br s, 3 H), 5.02 (d, 6 H), 4.98 (d, 6 H), 4.85 (d, 6 H), 4.54 (t, 6 H), 4.46–4.50 (m, 12 H), 4.24 (dd, 6 H), and 4.16 ppm (dt, 6 H); $^{13}$C-NMR ($D_2O$; 100 MHz) δ 167.7, 138.0, 137.1, 135.3, 129.9, 125.3, 122.0, 99.5, 76.2, 75.9,, 73.4, 72.6, 70.9, and 67.6 ppm. Anal. Calcd. for $C_{69}H_{69}N_3Na_{24}O_{111}S_{24}$·24$H_2O$·4$Na_2SO_4$: C, 16.45; H, 2.34; N, 0.83; S, 17.82. Found: C, 16.51; H, 2.17; N, 0.84, S, 18.17.

EXAMPLE 14

Step 1

Benzene-1,3,5-tricarboxylic Acid Tris{[3,5-bis-(β-D-cellobiosyloxymethyl)phenyl]amide}

To a solution of 802 mg (0.577 mmol) of 3, 5-bis-(hepta-O-acetyl-β-D-cellobiosyloxymethyl)phenylamine in THF (25 mL) containing 80.6 μL (1.28 mmol) of triethylamine was added 51.2 mg (0.193 mmol) of benzene-1,3,5-tricarboxylic acid chloride. The reaction mixture was stirred for 90 min, quenched with MeOH, diluted with $CH_2Cl_2$, and washed with $H_2O$. The organic phase was dried ($MgSO_4$) and concentrated to a light yellow solid. Purification was achieved by trituration from $CH_2Cl_2$/petroleum ether to provide 777 mg (94% yield) of product. A solution of 777 mg (0.180 mmol) of the compound in MeOH (25 mL) was treated with 8.1 mL (8.1 mmol) of 1N NaOH. After stirring for 2.5 h at 50° C., the reaction mixture was quenched at room temperature with 1N HCl (7.6 mL, 7.6 mmol). The solid was collected and purified by reverse phase chromatography (RP silica 60) using elution of MeOH/$H_2O$ (3:7) and then by Sephadex G-10 chromatography ($H_2O$ elution) to provide 262 mg (57% yield) of the title compound as a colorless solid, mp>171° C. (dec): $^{13}$C-NMR ($D_2O$, 100 Hz)

δ 165.3, 138.4, 137.2, 134.0, 130.0, 123.9, 119.9, 102.6, 101.7, 78.7, 75.9, 75.5, 74.6, 74.2, 73.1, 72.8, 70.6, 69.4, 60.5, and 60.0 ppm.

Step 2

Benzene-1,3,5-tricarboxylic Acid Tris{[3,5-bis-(hepta-O-sulfato-β-D-cellobiosyloxymethyl)phenyl]amide} Tetratetracontasodium Salt A solution of 139 mg (0.0543 mmol) of benzene-1,3,5-tricarboxylic acid tris{[3,5-bis-(β-D-lactosyloxymethyl)phenyl]amide} and sulfur trioxide trimethylamine complex (1.68 g, 12.07 mmol) in DMF (25 mL) was stirred at 70° C. for 3 days. The reaction mixture was quenched at room temperature with $H_2O$ and concentrated in vacuo. The residue was purified by Sephadex G-10 chromatography ($H_2O$ elution). Cation exchange was effected using a column of Dowex 50×8 strongly acidic resin (Na form) to provide 317 mg (85% yield) of the title compound as a tan solid, mp>180° C. (dec): partial $^1$H-NMR ($D_2O$; 400 MHz) δ 8.64 (s, 3 H), 7.67 (s, 6 H), 7.46 (s, 3 H), 5.02 (d, 6 H), 4.96 (d, 6 H), 4.64 (t, 6 H), and 3.88–4.01 (m, 12 H); $^{13}$C-NMR ($D_2O$; 100 MHz) δ 167.7, 138.0, 137.0, 135.3, 129.9, 125.1, 121.8, 99.8, 77.7, 77.5, 77.4, 77.0, 74.2, 73.5, 73.4, 72.9, 71.0, 67.6, 66.1 ppm; mass spectrum (electrospray) (m-zNa)/z 883.4 (m−8 Na)$^{8-}$, 738.2 (m−9 Na)$^{9-}$, 662.0 (m−10 Na)$^{10-}$, 599.5 (m−11 Na)$^{11-}$. Anal. Calcd. for $C_{105}H_{111}N_3Na_{42}O_{195}S_{42}$·42 $H_2O$ : C, 16.59; H, 2.58; N, 0.55; S, 17.71. Found: C, 16.47; H, 2.86; N, 0.45; S, 14.72.

What is claimed:

1. A compound of Formula I

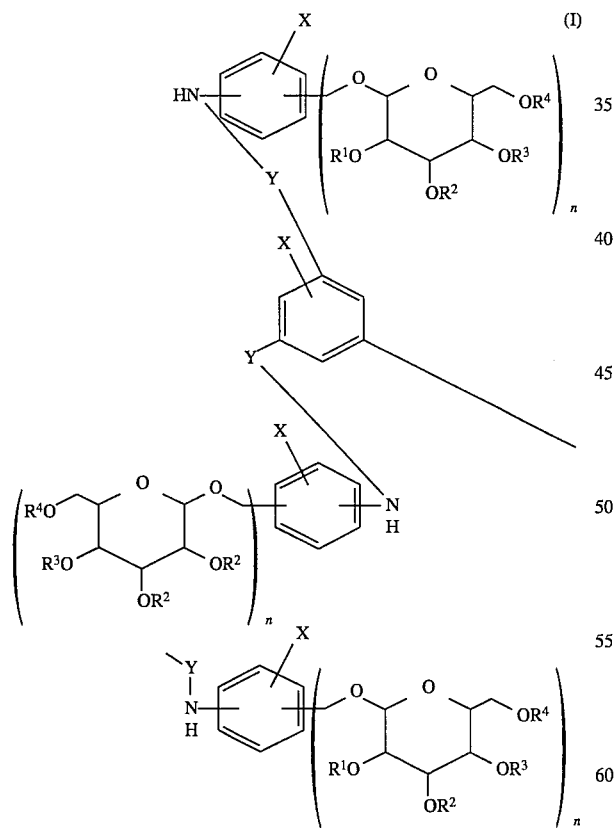

wherein n is 1 or 2;

each of $R^1$, $R^2$, $R^3$, and $R^4$ are, independently, H, $SO_3M$, or a glycoside having the structure:

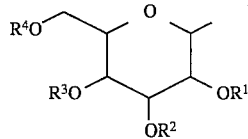

wherein $R^1$, $R^2$, $R^3$, and $R^4$ are as hereinbefore defined;

and each monosaccharide or oligosaccharide group having the structure

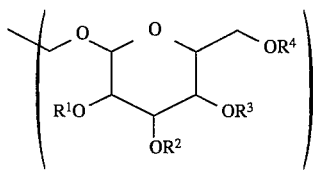

contains 1 to 3 glycoside groups, as hereinbefore defined;

M is lithium, sodium, potassium, or ammonium;

X is a halogen, lower alkyl having 1 to 6 carbon atoms, or lower alkoxy having 1 to 6 carbon atoms; and Y is carbonyl or sulfonyl; or a pharmaceutically acceptable salt thereof.

2. A compound according to claim 1 of Formula I:

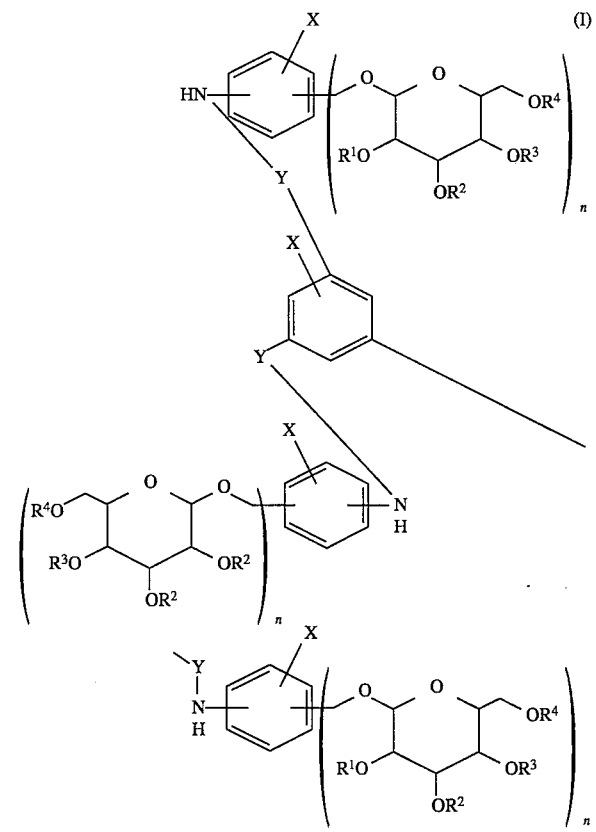

wherein n is 1 or 2;

each of $R^1$, $R^2$, $R^3$, and $R^4$ are, independently, H, $SO_3M$, or a glycoside having the structure:

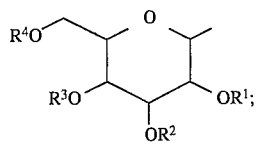

and each monosaccharide or oligosaccharide group having the structure

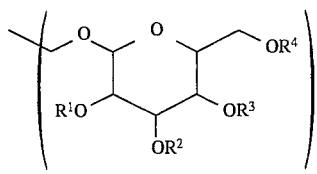

contains 1 or 2 glycoside groups;

M is lithium, sodium, potassium, or ammonium;

X is a halogen, lower alkyl having 1 to 6 carbon atoms, or lower alkoxy having 1 to 6 carbon atoms;

Y is carbonyl; or a pharmaceutically acceptable salt thereof.

3. A compound according to claim 1 which is benzene-1,3,5-tricarboxylic acid tris{[2-methyl-5-(tetra-O-sulfato-β-glucopyranosyloxymethyl)phenyl]amide} dodecasodium salt or a pharmaceutically acceptable salt thereof.

4. A compound according to claim 1 which is benzene-1,3,5-tricarboxylic acid tris {[2-methyl-5-(hepta-O-sulfato-β-cellobiosyloxymethyl)phenyl]amide} heneicosasodium salt or a pharmaceutically acceptable salt thereof.

5. A compound according to claim 1 which is benzene-1,3,5-tricarboxylic acid tris {[2-chloro-5-(hepta-O-sulfato-β-D-maltosyloxymethyl)phenyl]amide) heneicosasodium salt or a pharmaceutically acceptable salt thereof.

6. A compound according to claim 1 which is benzene-1,3,5-tricarboxylic acid tris[2-chloro-5-(hepta-O-sulfato-β-D-cellobiosyloxymethyl)phenyl]amide} heneicosasodium salt or a pharmaceutically acceptable salt thereof.

7. A compound according to claim 1 which is benzene-1,3,5-tricarboxylic acid tris {[2-chloro-5-(hepta-O-sulfato-β-D-lactosyloxymethyl)phenyl]amide} heneicosasodium salt or a pharmaceutically acceptable salt thereof.

8. A compound according to claim 1 which is benzene-1,3,5-tricarboxylic acid tris{[3,5-bis-(tetra-O-sulfato-β-D-glucosyloxymethyl)phenyl]amide} tetracosasodium salt or a pharmaceutically acceptable salt thereof.

9. A compound according to claim 1 which is benzene-1,3,5-tricarboxylic acid tris{[3,5-bis-(hepta-O-sulfato-β-D-cellobiosyloxymethyl)phenyl]amide} tetratetracontasodium salt or a pharmaceutically acceptable salt thereof.

10. A method of treating a human suffering from a condition which is characterized by excessive smooth muscle proliferation, the method comprising administering to the human an effective amount for reducing smooth muscle proliferation of the compound of the Formula I

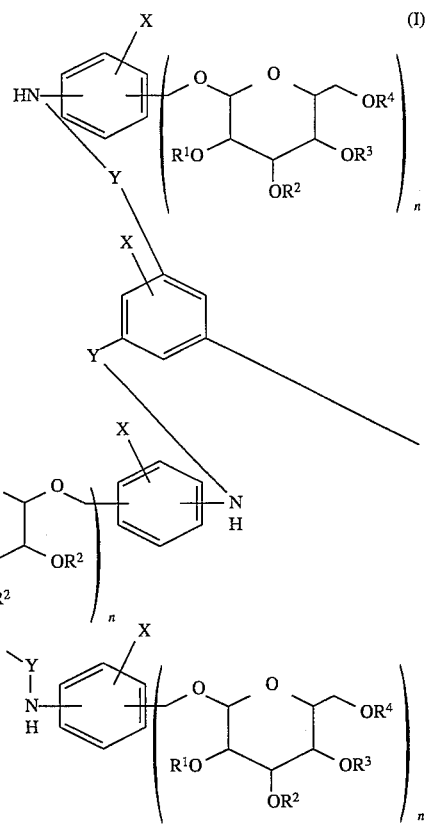

wherein n is 1 or 2;

each of $R^1$, $R^2$, $R^3$, and $R^4$ are, independently, H, $SO_3M$, or a glycoside having the structure:

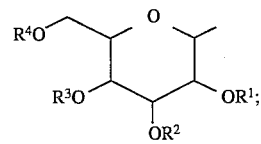

and each monosaccharide or oligosaccharide group having the structure

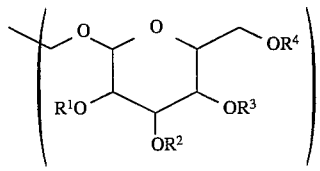

contains 1 to 3 sugar groups;

M is lithium, sodium, potassium, or ammonium;

X is a halogen, lower alkyl having 1 to 6 carbon atoms, or lower alkoxy having 1 to 6 carbon atoms;

Y is carbonyl or sulfonyl; or a pharmaceutically acceptable salt thereof.

11. A pharmaceutical composition comprising an effective amount for reducing smooth muscle proliferation of a compound of formula I

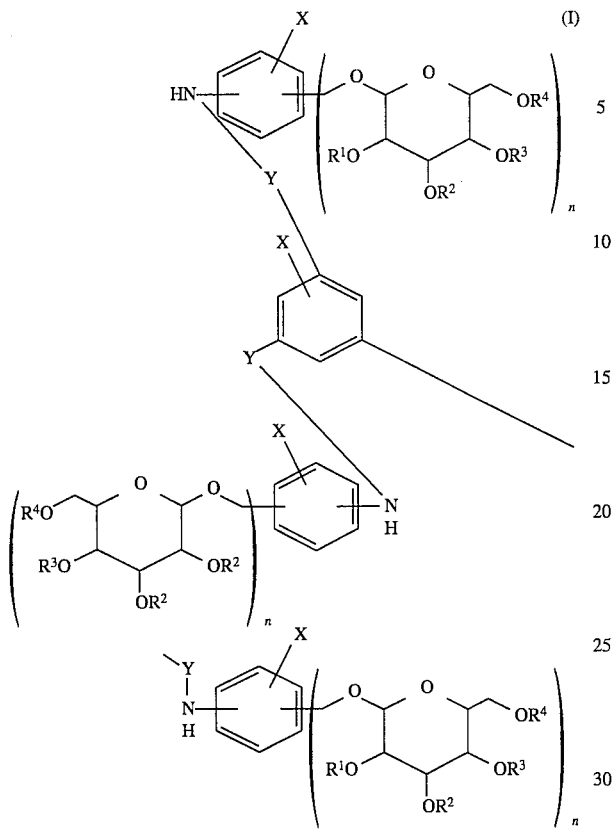

wherein
n is 1 or 2;
each of $R^1$, $R^2$, $R^3$, and $R^4$ are, independently, H, $SO_3M$, or a glycoside having the structure:

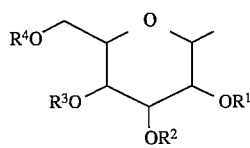

wherein $R^1$, $R^2$, $R^3$, and $R^4$ are as hereinbefore defined;
and each monosaccharide or oligosaccharide group having the structure

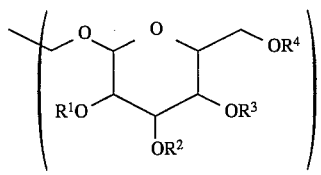

contains 1 to 3 glycoside groups, as hereinbefore defined;
M is lithium, sodium, potassium, or ammonium;
X is a halogen, lower alkyl having 1 to 6 carbon atoms, or lower alkoxy having 1 to 6 carbon atoms; and
Y is carbonyl or sulfonyl; or a pharmaceutically acceptable salt thereof, in combination with a pharmaceutically acceptable carrier.

\* \* \* \* \*